United States Patent

Schweikert et al.

[11] Patent Number: 5,925,684
[45] Date of Patent: Jul. 20, 1999

[54] STABLE CAROTENOID EMULSIONS SUITABLE FOR PARENTERAL ADMINISTRATION

[75] Inventors: Loni Schweikert, Altrip; Karl Kolter, Limburgerhof, both of Germany

[73] Assignee: BASF Aktiengesellschaft, Ludwigshafen, Germany

[21] Appl. No.: 08/813,977

[22] Filed: Mar. 10, 1997

[30] Foreign Application Priority Data

Mar. 11, 1996 [DE] Germany .............................. 196 09 476

[51] Int. Cl.$^6$ .......................... A61K 9/107; A61K 47/32; A61K 47/18
[52] U.S. Cl. .......................... 514/941; 514/938; 514/975; 424/400; 252/311; 252/312
[58] Field of Search .................................. 514/772.1, 941, 514/938, 975; 424/400; 252/311, 312

[56] References Cited

U.S. PATENT DOCUMENTS

| 4,107,343 | 8/1978 | Petricca . |
| 5,075,113 | 12/1991 | DuBois . |
| 5,350,773 | 9/1994 | Schweikert et al. .................... 514/763 |
| 5,472,706 | 12/1995 | Friedman et al. . |

FOREIGN PATENT DOCUMENTS

| 55 817 | 7/1982 | European Pat. Off. . |
| 100 459 | 2/1984 | European Pat. Off. . |
| 479 066 | 4/1992 | European Pat. Off. . |
| 551 638 | 7/1993 | European Pat. Off. . |
| 2 254 105 | 11/1972 | Germany . |
| 2 236 899 | 2/1974 | Germany . |
| 37 02 030 | 8/1988 | Germany . |
| 44 05 545 | 2/1994 | Germany . |
| 918 399 | 2/1963 | United Kingdom . |
| WO8421232 | 9/1994 | WIPO . |
| WO94/21231 | 9/1994 | WIPO . |

OTHER PUBLICATIONS

Grant & Hackh's Chemical Dictionary, 5th Ed p. 116.
Journal of Pharmaceutical Sciences, APhA, Benita et al., vol. 82, No. 11.
Chem. Abstr. J5 8162–517.
Chem. Abstr. JO 4026–670.
Biochimica et aBiophysica Acta, 111 (1992) 135–138, Grolier et al.

Primary Examiner—Edward J. Webman
Attorney, Agent, or Firm—Keil & Weinkauf

[57] ABSTRACT

A stable oil-in-water emulsion suitable for parenteral administration, containing less than 10% by weight lecithin, consisting of an aqueous phase and of an oil phase which is very finely dispersed by means of a physiologically tolerated emulsifier and which contains at least one carotenoid and is based on a physiologically tolerated oil or fat and comprises as emulsifier polyoxyethylene/polyoxypropylene block polymers and/or lecithin, and wherein the carotenoid is present in the oil phase in a concentration above the saturation solubility of the carotenoid in the oil or fat at room temperature.

9 Claims, No Drawings

STABLE CAROTENOID EMULSIONS SUITABLE FOR PARENTERAL ADMINISTRATION

The invention relates to oil-in-water carotenoid emulsions, ie. with an oil phase comprising dispersed carotenoid, in which the carotenoid concentration is higher than the saturation concentration at room temperature, and to a process for the preparation of these emulsions.

Carotenoids have antioxidant effects and are excellent oxygen free radical scavengers. The protective effect of carotenoids is utilized by nature in photosynthesis systems. Thus, chlorophyll is associated in green plants with β-carotene, which prevents oxidative damage to the photosynthesis system.

In higher organisms, such as humans, metabolic processes likewise result in aggressive oxygen free radicals which have been suggested to cause or promote certain diseases (eg. arthritis, cancer).

Carotenoids, especially β-carotene, occur in plant foodstuffs such as vegetables or lettuces and are taken into the human body with the food.

However, on the other hand, it is known that the proportion of carotenoids, which are as a rule of low solubility, absorbed can be very low. For example, little β-carotene is taken up by the human body from raw carrots. Unbalanced dietary habits make an additional contribution to only small amounts of carotenoids being taken in with the diet by certain groups in the population.

For this reason there is interest in the development of carotenoid formulations which are suitable for injections and make it possible rapidly to increase the carotenoid concentration in the body. A particular difficulty in this connection is the generally known poor dissolving properties of most carotenoids, which are completely insoluble in water and have only limited solubility in fats and oils.

The use of solutions of carotenoids as molecular dispersions in oils or oil-soluble substances is problematic for injections and entirely unsuitable for administration directly into the bloodstream because there is a risk of fat embolism.

There are several possibilities for converting carotenoids of low solubility into a form suitable for injections, for example the use of solubilizers which form micelles with β-carotene in aqueous systems, or the preparation of β-carotene emulsions, in which case it has not hitherto been possible as a rule to obtain higher concentrations of β-carotene, because of the low oil-solubility. It is of course generally necessary to ensure that all the components are physiologically well tolerated.

For this purpose, EP-B-055 817 and EP-A-0 479 066 describe the preparation of carotenoid solubilizates with nonionic emulsifiers, especially of the ethoxylated fatty acid type. Although these micellar solutions are suitable in principle for injection, the use of ethoxylated fatty acids may lead to serious intolerance reactions (anaphylactic shock).

DE 2236899 and DE 2254105 describe carotenoid-containing emulsions which may contain up to 4% carotenoid (bixin, crocetin, xanthophyll or zeaxanthin). Necessary for the preparation of these emulsions are, as emulsifiers, compounds of tris(hydroxymethyl) aminomethane and C 9-C 20-fatty acids and, as diluents, high concentrations of a hydrophilic organic solvent or a second emulsifier. These auxiliaries are poorly tolerated at the stated concentrations and do not permit parenteral administration to humans.

Japanese Patent 04026670 describes a vitamin preparation which contains a carotenoid as stabilizer. The carotenoid concentration in this case is limited to the saturation solubility in the oil-soluble substance employed (vegetable oils, hydrocarbons, paraffin).

The preparation of a carotenoid-containing fat emulsion consisting of β-carotene or zeaxanthin, soybean oil (10%), soybean lecithin (1.2%), glycerol (2.5%) and water is described by P. Grolier, V. Azais-Braesco, L. Zelmire and H. Fessi in Biochimica et Biophysica Acta 1111 (1992) 135–138. The authors state that an impediment that could not be overcome was the low oil-solubility of said carotenoids. Although the initial concentration of β-carotene in the oil was 0.12%, the concentrations fell and after preparation were less than 0.0037%. This means that β-carotene precipitated or decomposed during the preparation. It was not possible to prepare any fat emulsions with zeaxanthin because the oil-solubility is even lower.

Emulsions with vitamins A, D and E are known in the animal feed sector and from various patents (EP 100 459, JP 581 625 17). Since these vitamins have good oil-solubility, they can in principle be incorporated in an emulsion. The difficulties in this case lie in the production of stable preparations, especially when parenterally tolerated emulsifiers are to be employed and cosolvents such as glycerol, propylene glycol or polyethylene glycol in higher concentrations are to be dispensed with.

Fat emulsions constitute in principle a thermodynamically unstable system which reacts very sensitively to changes. Even slight changes in the nature and amount of active substances or auxiliaries may lead to the entire system being unstable (J. Pharm. Sci. 82 (1993) 1069–78). This is of crucial importance because fat emulsions for parenteral administration must meet special requirements in order not to endanger the life of the patients. Particularly important in this connection are the particle size—particles larger than 1 μm may lead to fat embolism—the systemic and local tolerability and the hemolytic activity. For tolerability reasons, a parenteral fat emulsion must have approximately the osmolarity of blood, about 300 mosmol. If the osmolarity is lower, the blood corpuscles rupture on administration, and if it is higher they lose water and thus shrink. Both of these cause damage. This fact also prohibits parenteral use of emulsions which are known for oral administration and contain large amounts of polyols, such as glycerol, in humans.

PCT Applications WO 94/21231 and WO 94/21232 describe β-carotene-containing emulsions with a high glycerol content (30 to 90%). These preparations do not, because of the high glycerol concentration, meet the requirement of isotonicity with blood and are therefore not tolerated on parenteral use without dilution. On the other hand, dilution has the disadvantages that the volume of liquid injected increases and the emulsion may be changed by the dilution, eg. become unstable or the droplet size increases in an uncontrolled manner. This is unacceptable for reasons which have already been described (danger of fat embolism).

It is an object of the present invention to develop systems which contain well-tolerated dispersants, make high carotenoid concentrations possible, are stable on storage and make the requirement of isotonicity with blood.

We have found that this object is achieved by stable oil-in-water emulsions suitable for parenteral administration, consisting of an aqueous phase and of an oil phase which is very finely dispersed by means of a physiologically tolerated emulsifier and has particle sizes below 1 μm, and which contains at least one carotenoid and is based on a physiologically tolerated oil or fat, wherein the emulsion comprises less than 10% by weight of glycerol and comprises as emulsifier polyoxyethylene/polyoxypropylene block copolymers and/or lecithin, and wherein the carotenoid is present in the oil phase in a concentration above the saturation solubility of the carotenoid in the oil or fat at room temperature.

In the present invention it is possible in principle entirely to dispense with glycerol, or the glycerol concentration can be less than 10% by weight. The glycerol concentration is preferably from 1 to 3% by weight to set up isotonicity with blood.

The vehicles for the carotenoids in the oil phase are oils approved for injections, as listed in the textbook Pharmazeutische Technologie, edited by H. Sucker, P. Fuchs and P. Speiser, 2nd edition (1991), pages 459 and 504, eg. soybean oil or medium chain-length triglycerides like those present in coconut oil. It has additionally been found that vitamin E or A or derivatives thereof can be used as outstanding vehicles for carotenoids, especially if the aim is to prepare vitamin-containing carotenoid emulsions.

Particularly suitable as oily vehicle is vitamin E (tocopherol) which likewise acts as antioxidant, and oily derivatives thereof, such as tocopherol acetate. Use thereof has the advantage that a preparation entirely free of edible fats and oils can be produced and thus there is no worry about adverse effects of a fat content (increase in the triglyceride level in the blood).

Suitable carotenoids are all carotenoids which dissolve in oil at elevated temperature, eg. canthaxanthin, citranaxanthin, zeaxanthin, apocarotenal, apocarotenoic acid derivatives such as ethyl apocarotenoate, and mixtures thereof. However, β-carotene, lycopene, astaxanthin or a mixture thereof is particularly suitable for use as antioxidant or free radical scavenger.

It is also possible to add other water-soluble active substances to the aqueous phase, such as water-soluble vitamins and trace elements. A suitable additive is, in particular, vitamin C or sodium ascorbate, both of which likewise act as antioxidant in the body. It may be advantageous for increasing the microbiological stability to add limited amounts (max. 10%) of ethyl alcohol or other tolerated preservatives such as thimerosal or chlorocresol etc. to the injection emulsion.

Suitable emulsifiers are conventional physiologically tolerated dispersants from the group of propylene oxide/ethylene oxide block copolymer or the group of lecithins, and mixtures of these two groups, with polyoxyethylene/polyoxypropylene block copolymers being preferred. The polyoxyethylene/polyoxypropylene block copolymers to be used according to the invention—also called poloxamers—are compounds of the formula

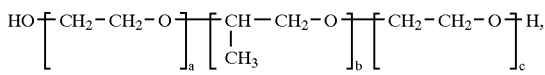

where a and c are from 2 to 130 and b is from 15 to 67 units. A particularly suitable product is one in which a and c are about 80 and b is about 30. The effect of these emulsifiers can be enhanced by coemulsifiers such as mono- or diglycerides, ascorbyl fatty acid esters or fatty acids and fatty acid salts.

The solubility of most carotenoids in oils is so low that 0.05–0.1% is scarcely exceeded at room temperature. The carotenoid is therefore dissolved in the vehicle by briefly heating at above 120° C., by which means the solubility is considerably increased. The carotenoid concentration in the oily vehicle can then be from 0.2% to 50% by weight and is preferably from 10% to 20% by weight.

It is possible, starting from these carotenoid/oil or carotenoid/vitamin mixtures, to prepare oil-in-water emulsions which have a carotenoid content of at least 0.1%. The upper limit of the carotenoid concentration achievable in the emulsion is limited not least by the total content of dispersed phase in the injection emulsion, which should typically not exceed 50%. This results in a maximum achievable carotenoid concentration of 25% in the finished injection emulsion. As a rule, the carotenoid content will not exceed 10% of the weight of the emulsion.

Accordingly, the preparations according to the invention contain, based on the finished emulsion, 0.1–10, preferably 0.1–5, % by weight carotenoid, preferably β-carotene, 0.2–50, preferably 1–20, % by weight of oily vehicle, 0.1–15, preferably 1.0–10% by weight, emulsifier and the remainder aqueous phase, which may contain from 0.001 to 1% by weight minerals such as Cu, Se, Zn or Mn salts and, if required, 5 other water-soluble vitamins such as vitamin C and vitamins $B_1$, $B_2$, $B_6$ and $B_{12}$.

The injection emulsions according to the invention may also contain in addition conventional antioxidants such as butylated hydroxytoluene, butylated hydroxyanisols, tocopherol or ascorbyl palmitate in conventional amounts, ie. from 0.01 to 2% by weight, to increase further the stability of, for example, the oily vehicle.

Surprisingly, such supersaturated carotenoid emulsions are stable for a long time, ie. there is no recrystallization of the active substance or coalescence of emulsion droplets. Like all injection emulsions, the emulsions according to the invention must have a high degree of fineness (no particle larger than 1 μm). The emulsions can be prepared using conventional technologies suitable for preparing an emulsion with the required degree of fineness.

It is generally true that the heating of the carotenoid at, for example, 120–250° C. in the oil should be as brief as possible and it should be cooled to room temperature or near room temperature as quickly as possible after dissolution is complete.

As a rule, this takes place by emulsifying the hot oil solution in the aqueous phase which is initially at room temperature or slightly elevated temperature.

The emulsification can be carried out continuously or batchwise.

In the batchwise procedure, for example, water for injection which contains the dispersant and, where appropriate, physiologically tolerated alcohols such as sorbitol, xylitol or glycerol is maintained at room temperature or a slightly elevated temperature, eg. up to 50° C. The carotenoid/oil solution is stirred into the aqueous phase with a high-speed stirrer, eg. with an Ultraturrax®, and subsequently the resulting emulsion is homogenized with a high-pressure homogenizer.

In the continuous procedure, which is preferred, the method is similar to that described in DE-A-37 02 030, to which express reference is made concerning the apparatus and the procedure and whose statements are to be regarded as integrated in the present description with the proviso of the modification described below.

The essential components of this process are two mixing chambers. The first mixing chamber is used for rapidly dissolving the carotenoid in a water-miscible organic solvent together with an edible oil, and with an emulsifier, where appropriate under pressure, at from 50° C. to 240° C., and immediately vigorously mixing the resulting solution in the second mixing chamber with an aqueous solution of a protective colloid, whereupon the solvent is transferred into the aqueous phase, and the hydrophobic oil phase in which the carotenoid is dissolved results as microdisperse phase. The resulting two-phase mixture is then freed of solvent and water to result in a powdered preparation.

This process is modified to prepare the injection solution according to the invention in such a way that a colloid-free aqueous phase, which expediently contains the emulsifier, is turbulently mixed with a hot solution of the carotenoid in the mixture of oil and water-miscible organic solvent. Where necessary, the emulsion can subsequently be homogenized with a high-pressure homogenizer. The amount of water-miscible solvent in the first mixing chamber, preferably ethyl alcohol, is chosen so that a physiologically tolerated concentration of, for example, 10% by weight is not exceeded in the resulting injection solution, where appropriate after dilution. Other conventional water-soluble ingredients in injection solutions, such as pH regulators, isotonicizing agents, salts or other active substances such as vitamin C, are either mixed in the aqueous phase before preparing the emulsion or are added after the emulsion is finished.

In place of the preparation of the carotenoid solution in the first mixing chamber, it is also possible to pass a carotenoid/oil suspension continuously through a heat exchanger and continue processing as described above.

The carotenoid emulsion is dispensed in a conventional way under sterile conditions into infusion bottles, vials, ampoules or prefilled syringes. Where necessary, these can be subjected to a gentle thermal microbe-reducing process.

The highly concentrated carotenoid emulsions are suitable for direct parenteral administration or can be diluted before administration with compatible aqueous infusion solutions or fatty emulsions for parenteral alimentation.

Besides parenteral administration, use orally or dermally is also possible, in which case high absorption through the mucous membrane or skin is to be expected because of the supersaturation with β-carotene.

It has been possible to date to provide antioxidant preparations containing β-carotene, tocopherol or tocopherol acetate and ascorbic acid in the form of tablets or capsules for oral administration. These antioxidant preparations are attributed with numerous effects such as prevention of myocardial infract, stroke, cancer, macular degeneration, Parkinsonism, Alzheimer's disease etc. The present invention makes it possible for these substances to be administered parenterally in the preparation either directly or else after dilution. However, it is possible to prepare in a similar manner not only antioxidant preparations but also β-carotene-containing multivitamin solutions for injections or infusions.

In the following examples, the emulsifier was added to the aqueous phase. However, addition to the lipophilic phase is also possible in principle, especially when the emulsifier dissolves therein.

EXAMPLE 1

418 ml of demineralized water (water for injections) are mixed with 40 g of propylene oxide/ethylene oxide block copolymer (Lutrol® F 68 from BASF, Poloxamer 188) and 10 g of glycerol in a 1 l beaker and heated to 45° C. in a waterbath. 32 g of a 30% strength β-carotene dispersion in fractionated coconut oil (Miglyol 810) in a 100 ml round-bottom flask are briefly heated to 180° C. with stirring, whereupon the β-carotene dissolves.

This oily solution is emulsified into the aqueous phase. The emulsification takes place at 45° C. using an Ultraturrax® (7000–8000 rpm) for 8 min. The emulsion is then homogenized at 1000 bar. The finished emulsion, which has a β-carotene content of 1.6% and an average particle size of 210 nm, is mixed with 0.1% thiomersal preservative and dispensed into 10 ml vials.

EXAMPLE 2

The technique of mixing chamber micronization indicated in DE-A 37 02 030 is used initially to mix in the first mixing cell a 4.4% strength ethanolic β-carotene dispersion which contains 20% tocopherol with ethanol at 220° C. under pressure (pressure control valve set at 35 bar), the temperature set up in the mixing cell under these given conditions being 190° C. The β-carotene dissolves during this. The flow rates are 2 kg/h for dispersion containing active substance and 2.5 kg/h for pure ethanol.

This hot solution is then mixed turbulently in the downstream second mixing cell with the aqueous phase, which is pumped in at a rate of 27 kg/h. The aqueous phase contains besides demineralized water (water for injections), 3.4% ascorbic acid, 0.6% propylene oxide/ethylene oxide block copolymer (Lutrol F 68 =poloxamer 188), and the pH was adjusted to 7.5 with 1 M NaOH.

Mixing in the second mixing chamber results in microdisperse droplets which contain β-carotene and tocopherol and have an average particle size of 210 nm. The resulting emulsion contains 15% ethanol and is diluted with demineralized water, to obtain a tolerated injection preparation, so that the ethanol content reaches 8%. The β-carotene content in the diluted dispersion is 0.15%, the tocopherol content is 0.68% and the ascorbic acid content is 1.58%.

EXAMPLE 3

14 g of glycerol, 35 g of Lutrol® F 68 (BASF Aktiengesellschaft), 35 g of ascorbyl palmitate and 19.67 g of sodium ascorbate are dissolved 550.8 g of water for injections at 60° C. The pH of the solution is adjusted to 7.4 with NaOH. A mixture of 56 g of fractionated coconut oil (Miglyol 812) and 14 g of tocopherol acetate is heated to 180° C. in a round-bottom flask, 7 g of β-carotene are added under nitrogen, and the mixture is stirred until the β-carotene has completely dissolved. The resulting β-carotene solution is emulsified twice into the aqueous phase using an Ultra-Turrax® at 3000 rpm. This preemulsion is subsequently further emulsified through a homogenizer under 1000 bar and dispensed into vials. The content of β-carotene is 1.0% by weight, of tocopherol acetate is 2.0% by weight and of sodium ascorbate is 2.8% by weight. The average particle size is 200 nm. The β-carotene concentration is 10% of the weight of the oil phase.

EXAMPLE 4

The emulsion is prepared as described in Example 3 but Miglyol 812 is replaced by tocopherol acetate, and no sodium ascorbate is used. The lipophilic phase thus consists entirely of tocopherol acetate. The content, based on the complete emulsion, of β-carotene is 1.0% by weight and of tocopherol acetate is 10.0% by weight. The particle size is 250 nm. The β-carotene concentration in the oil phase is 10% by weight.

EXAMPLE 5

14 g of glycerol, 35 g of Lutrol F68, 3.5 g of ascorbyl palmitate, 7.0 g of sodium ascorbate, 0.7 g of sodium riboflavin-5-phosphate×2 $H_2O$, 0.7 g of thiamine hydrochloride, 2.1 g of nicotinamide and 0.7 g of pyridoxine hydrochloride are dissolved in 562.8 g of water for injections at 60° C. The pH is adjusted to 7.4 with 1 molar NaOH. A mixture of 66.5 g of fractionated coconut oil (Miglyol 812) and 3.5 g of tocopherol acetate is heated in a round-bottom flask to 180° C., 3.5 g of β-carotene are added under nitrogen, and the mixture is stirred until the β-carotene has completely dissolved. The oily solution is emulsified into the aqueous solution of the vitamins using an Ultra-Turrax® at 3000 rpm. Further emulsification to a fine-particle emulsion takes place by two passages through a homogenizer under 1000 bar. The emulsion is subsequently cooled to room temperature and dispensed into vials.

Content, based on the complete emulsion, of

β-carotene: 0.5% by weight tocopherol acetate: 0.5% by weight sodium ascorbate: 1.0% by weight Na riboflavin-5-phosphate: 0.1% by weight thiamine HCl: 0.1% by weight nicotinamide: 0.3% by weight pyridoxine HCl: 0.1% by weight The particle size is 200 nm. The β-carotene concentration is 5% of the weight of the oil phase.

We claim:

1. A stable oil-in-water emulsion suitable for parenteral administration which consists essentially of an aqueous phase and a physiologically tolerated oil phase which is very finely dispersed by means of a physiologically tolerated emulsifier and has particle sizes below 1 μm, and which contains at least one carotenoid selected from the group consisting of β-carotene, lycopene, astaxanthin, canthaxanthin, citranexanthin, zeaxanthin, apocarotenal and apocarotenoic acid, wherein the emulsion contains less than 10% by weight glycerol and contains as emulsifier polyoxyethylene/polyoxypropylene block copolymers and/or lecithin, and wherein the carotenoid is present in the oil phase in a concentration above the saturation solubility of the carotenoid in the oil or fat at room temperature and the carotenoid content is from 0.1 to 10% by weight of the total stable oil-in-water emulsion.

2. The stable emulsion of claim 1, which contains from 1 to 3% by weight glycerol.

3. The stable emulsion of claim 1, which contains as a coemulsifier mono- or diglycerides, ascorbyl fatty acid esters or fatty acids or fatty acid salts.

4. The stable emulsion of claim 1, wherein the oil in the oil phase is soybean oil, a medium chain-length triglyceride, tocopherol or tocopheryl ester.

5. The stable emulsion of claim 1, wherein the carotenoid is beta-carotene.

6. The stable emulsion of claim 1, wherein the oil phase comprises beta-carotene and tocopherol or tocopheryl ester and the aqueous phase comprises ascorbic acid or sodium ascorbate.

7. The stable emulsion of claim 1, wherein the oil phase comprises other oil-soluble vitamins and the aqueous phase comprises other water-soluble vitamins and trace elements.

8. The stable emulsion of claim 1, which contains from 0.1 to 5% by weight carotenoid and from 0.2 to 50% by weight of oil or fat, based on the complete emulsion.

9. The stable emulsion of claim 1, which comprises as emulsifier polyoxyethylene/polyoxypropylene block copolymers.

* * * * *